US009963477B2

(12) United States Patent
Essayem et al.

(10) Patent No.: US 9,963,477 B2
(45) Date of Patent: May 8, 2018

(54) METHOD FOR THE ISOMERISATION OF GLUCOSE INTO FRUCTOSE

(75) Inventors: Nadine Essayem, Saint Just Chaleyssin (FR); Rodrigo Lopes De Souza, Sen. Camara Rio De Janeiro (BR); Franck Rataboul, Lyons (FR); Cyril Feche, Leyment (FR); Dilson Cardoso, Sao Carlos (BR); Demian Patrick Fabiano, Ouro Branco (BR)

(73) Assignees: CENTRE NATIONAL DE LA RECHERCHE SCIENTIFIQUE (C.N.R.S.), Paris (FR); UNIVERSITE CLAUDE BERNARD LYON I, Villeubanne (FR)

( * ) Notice: Subject to any disclaimer, the term of this patent is extended or adjusted under 35 U.S.C. 154(b) by 83 days.

(21) Appl. No.: 14/241,213

(22) PCT Filed: Aug. 24, 2012

(86) PCT No.: PCT/EP2012/066546
§ 371 (c)(1),
(2), (4) Date: Dec. 5, 2014

(87) PCT Pub. No.: WO2013/030132
PCT Pub. Date: Mar. 7, 2013

(65) Prior Publication Data
US 2015/0126731 A1  May 7, 2015

(30) Foreign Application Priority Data
Aug. 26, 2011 (FR) .................................. 11 57575

(51) Int. Cl.
*C07H 1/00* (2006.01)
*C07D 307/46* (2006.01)
*C07H 3/02* (2006.01)

(52) U.S. Cl.
CPC ............ *C07H 1/00* (2013.01); *C07D 307/46* (2013.01); *C07H 3/02* (2013.01)

(58) Field of Classification Search
CPC .......... C07H 1/00; C07H 3/02; C07D 307/46
USPC ......................................... 536/125; 549/488
See application file for complete search history.

(56) References Cited

U.S. PATENT DOCUMENTS

| 2,929,823 A | 3/1960 | Garber et al. |
| 2004/0122275 A1* | 6/2004 | Levin ........................ C07C 1/20 585/639 |
| 2011/0207923 A1* | 8/2011 | Moliner-Marin .... C07D 307/58 536/125 |

FOREIGN PATENT DOCUMENTS

| FR | 2862973 | 6/2005 |
| WO | WO-92/10486 | 6/1992 |
| WO | WO 2010/101024 | 9/2010 |

OTHER PUBLICATIONS

International Search Report for PCT/EP2012/066546 dated Sep. 7, 2012.
Lima et al: "Isomerization of d-glucose to d-fructose over metallosilicate solid bases", Applied Catalysis A: General, Elsevier Science, Amsterdam, NL, vol. 339, No. 1, (Jan. 17, 2008), pp. 21-27.
Moreau C et al:"Isomerization of glucose into fructose in the presence of cation-exchanged zeolites and hydrotalcites", Applied Catalysis A: General, Elsevier Science, Amsterdam, NL, vol. 193, No. 1-2, (Feb. 28, 2000), pp. 257-264.
Atsushi Takagaki et al: "A one-pot reaction for biorefinery: combination of solid acid and base catalysts for direct production of 5-hydroxymethylfurfural from saccharides", Chemical Communications, No. 41, (Jan. 1, 2009), p. 6276-6278.
Dahai Yu et al: "Microwave irradiation-assisted isomerization of glucose to fructose by immobilized glucose isomerase", Process Biochemistry, Elsevier Ltd., vol. 46, (2011), pp. 599-603.
Yuriy Roman-Leshkov et al: "Mechanism of Glucose Isomerization Using a Solid Lewis Acid Catalyst in Water", Biomass Conversion, Agnew .Chem. Int. Ed., vol. 49, (2010), pp. 8954-8957.

* cited by examiner

*Primary Examiner* — Yih-Horng Shiao
(74) *Attorney, Agent, or Firm* — B. Aaron Schulman, Esq.; Stites & Harbison, PLLC

(57) ABSTRACT

The invention relates to a method for the isomerization of glucose into fructose in water in the presence of a solid base catalyst characterized by its reversibility of $CO_2$ adsorption at a low temperature, the catalyst being a catalyst comprising at least one supported or non-supported lanthanide oxide or a molecular sieve based on silicon containing the organic template thereof. The invention also relates to a method for preparing HMF from glucose, comprising the isomerization of glucose into fructose.

6 Claims, 4 Drawing Sheets

METHOD FOR THE ISOMERISATION OF GLUCOSE INTO FRUCTOSE

The present invention relates to a method for isomerisation of glucose into fructose. The present invention also relates to a method for preparing HMF (5-hydroxymethylfurfural) from glucose comprising a step for isomerisation of glucose into fructose.

Fructose has many applications, notably within the scope of the food industry, fructose having a greater sweetening power than glucose, and in the preparation of intermediates, for example HMF, for preparing polymers, notably polyamides or polyesters. However, the production of fructose remains still low relatively to the production of glucose.

Methods have been developed for allowing the preparation of fructose by isomerisation of glucose. The usual method is an enzymatic method, the isomerisation of glucose into fructose being catalyzed by an immobilized enzyme, xylose isomerase. However, it is necessary to apply substantial amounts of enzyme and the cost related to this method is high. Further, the reaction time for obtaining conversion and a suitable fructose yield is very long.

In order to improve this enzymatic method, it was proposed (Yu et al., Process Biochemistry, 2011, 46, 599-603) to apply it under microwave irradiation. However, the cost related to this type of method remains high relatively to the obtained results.

Methods not applying micro-organisms have also been developed. Methods applied in the presence of sodium hydroxyde as a catalyst are notably known. However, the obtained results remain not very satisfactory notably because of a rapid loss of selectivity over time due to secondary reactions of the aldolisation type. On the other hand, homogeneous bases generate aqueous effluents to be reprocessed. Heterogeneous catalysis methods have also been proposed. The use of potassium aluminate for catalyzing the reaction of isomerisation of glucose into fructose is notably known from FR2862973. However, the obtained results in terms of yield, conversion and selectivity remain low. The use of zeolite or hydrotalcite (catalyst based on aluminium and magnesium) as a catalyst for the isomerisation reaction is also known from Moreau et al. (Applied Catalysis A: General, 193, 2000, 21-27). However the best fructose selectivities (90%) are obtained for low glucose conversions (10 to 20%). The use of metallosilicates as a catalyst for the isomerisation reaction is also known from Valente et al. (Applied Catalysis A: General, 339, 2008, 21-27). Methods have also been developed in acid catalysis (Davis et al., Angew. Chem. Int. Ed., 2010, 49, 8954-8957) which use Sn-Beta catalysts. The results obtained by these methods are however not good enough for competing with the present enzymatic method.

Finally, the preparation of HMF from glucose in a single step is known from Ebitani et al. (Chem. Commun., 2009, 6276-6278) comprising the isomerisation of glucose into fructose in the presence of a solid basic catalyst and the dehydration of the fructose into HMF in the presence of a solid acid catalyst.

However, these different methods have the drawback of being too expensive or of not having good results in terms of conversion of the glucose, of fructose yield and fructose selectivity.

The object of the present invention is to provide a method for isomerisation of glucose into fructose which may be industrialized and which may be applied at a reduced cost.

Another object of the present invention is to provide a method having good results in terms of conversion of glucose, of fructose yield and fructose selectivity.

Further another object of the present invention is to provide a method for isomerisation of glucose into fructose with which good results may be obtained in terms of yield, conversion and selectivity within a reduced time.

Another object of the invention is to provide such a method which is more robust than enzymatic methods, which are sensitive to many factors such as pH, temperature, presence of inhibitors, and which may therefore be more easily applied even on raw materials of variable purity stemming from biomass.

Another object of the present invention is also to provide a method for preparing HMF from glucose.

Other objects will further become apparent upon reading the following description.

All the drawbacks of the prior art are solved by the present invention which relates to a method for isomerisation of glucose into fructose in water in the presence of a solid basic catalyst, preferentially used without any thermal decarbonation activation, characterized by the reversibility of the $CO_2$ adsorption isotherms at low temperature, notably at 30° C. and preferably by a differential $CO_2$ adsorption heat, measured at 30° C., comprised between 60 and 110 kJ·mol$^{-1}$, preferably between 75 and 95 kJ·mol$^{-1}$, the catalyst being a catalyst comprising one supported or non-supported lanthanide oxide or a molecular sieve based on silicon containing its organic template.

Preferably, the catalyst is selected from solid weak base catalysts. These weak bases are characterized by $CO_2$ adsorption differential heats measured at 30° C. between 60 and 110 kJ·mol–$^1$, preferably between 75 and 90 kJ·mol$^{-1}$. These catalysts may be used without any thermal decarbonation activation, which is the main drawback which limits the application of usual basic catalysts on an industrial scale.

The $CO_2$ adsorption reversibility is notably expressed by resistance of the catalyst to poisoning by $CO_2$. This property is not conditioned by a preliminary activation. One should be actually aware that generally catalysts such as those used in the prior art which include basic sites, when they are left in ambient air, are poisoned with $CO_2$, the latter binding onto the basic sites of the catalyst in order to form carbonated species. By basic sites are meant a species containing a pair of electrons which may be transferred to an acid molecule. Usually, it is therefore necessary to pretreat these catalysts for example at a high temperature, in order to activate them and use them in a decarbonated reaction medium or subsequently to thermal activation, to rehydrate them so as to limit inhibition of the basic sites of the solid by trace amounts of atmospheric $CO_2$. On the other hand, the catalysts of the invention do not require any pretreatment, notably high temperature pretreatment.

The reversibility of $CO_2$ adsorption by a catalyst may be determined by calorimetry coupled with measurements of $CO_2$ adsorption isotherms (total and reversible adsorption) by volumetric measurement. $CO_2$ adsorption measurements are conducted by means of a calorimeter, notably a Tian Calvet calorimeter, and they are coupled with measurements of $CO_2$ adsorption isotherms by means of glass volumetric equipment equipped with a precision pressure gauge. The solid, introduced into the glass cell, is placed in the calorimetry held at the measurement temperature (30° C.) after having been treated in vacuo at this temperature until a suitable vacuum (10$^{-5}$ torrs) is obtained or at a higher temperature. The $CO_2$ is introduced in little increments at 30° C., the released heat is measured at each $CO_2$ dose just like the equilibrium temperature. The adsorption isotherm is determined up to the equilibrium pressure of 1 torr. After measurement of the first isotherm (total adsorption), a second isotherm is obtained (reversible adsorption) after having treated the solid catalyst in vacuo at 30° C. for 15 hours.

The catalysts supporting a supported or non-supported lanthanide oxide or a molecular sieve based on silicon containing their templates (notably CTA: cetyltrimethylammonium bromide) used in the invention are therefore those which have this $CO_2$ adsorption reversibility at 30° C. associated with an adsorption differential heat comprised between 60 and 110 kJ·mol$^{-1}$, preferably between 75 and 90 kJ·mol$^{-1}$.

Thus, and advantageously, the method of the invention does not comprise any pretreatment of the catalyst before use, intended for re-activating notably high temperature pretreatment catalyst.

Preferably, the resistance characteristic of the catalyst to $CO_2$ poisoning is expressed by the fact that the basic force of the catalyst is found between chemisorption and physisorption. Preferably at least 50% of the basic sites of the catalyst, without any form of pretreatment, notably without any high temperature pretreatment, have a $CO_2$ adsorption heat comprised between 60 and 110, preferably between 75 and 90 kJ·mol$^{-1}$. By <<$CO_2$ adsorption differential heat>>, is meant the molar heat released by adsorption of infinitesimal doses of $CO_2$, at constant temperature, on the catalyst initially in vacuo in a calorimeter of the Tian Calvet type. The values of $CO_2$ adsorption differential heats correspond to the value of the plateau of the curve representing the variation of the differential heats (Q diff kJ·mol$^{-1}$) versus the amount of adsorbed $CO_2$ if the basic solid has sites with homogeneous basic force. If the differential heats decrease with $CO_2$ recovery, the relevant value is the average of the adsorption differential heats with 50% $CO_2$ recovery.

The catalyst may be selected from lanthanide oxides, either supported or not, possibly hydroxylated and/or carbonated, from mixed lanthanide oxides with other metals, either supported or not, possibly hydroxylated and/or carbonated, or from molecular sieves based on silicon containing their organic template.

In an embodiment, the catalyst consists of a lanthanide oxide, preferably an La oxide, either supported or non-supported.

The lanthanides may be oxidized to various degrees; they may be partly hydroxylated and/or carbonated. Mention may notably be made of: $La_2O_3$, $La(OH)_3$ on coal, $La_2O_{3-x-y}(CO_3)_x(OH)_{2y}$, a formula in which x may be 0, 1, 2 or 3, for example 0, 1 or 2, y may be 0, 1, 2 or 3 with $0 \leq x+y \leq 3$.

In an embodiment, the catalyst comprises a lanthanide oxide, preferably La oxide, either supported or not. In a preferred embodiment, this catalyst, either supported or not supported is a mixed lanthanide oxide preferably of La, with other metals, notably alkaline or earth alkaline metals, e.g. Mg. Mention may be made of the mixed oxide of La and Mg, e.g. MgLaO. These mixed oxides may comprise a partly hydroxylated and/or carbonated lanthanide oxide, for example of the formula above, $La_2O_{3-x-y}(CO_3)_x(OH)_{2y}$, and for example with a Mg oxide (e.g. MgO).

By lanthanides, or rare earths, (Ln) are meant chemical elements selected from the group formed by scandium, yttrium and chemical elements with an atomic number from 57 to 71, preferably the chemical elements selected in the group formed by scandium and the chemical elements with atomic number from 57 to 71, preferably the chemical elements with an atomic number from 57 to 71. Advantageously, the lanthanides are selected from cerium (Ce), lanthanum (La), praseodymium (Pr), neodymium (Nd), yttrium (Y) and gadolinium (Gd), samarium (Sm) and holmium (Ho), preferably cerium (Ce), lanthanum (La), praseodymium (Pr), neodymium (Nd) and gadolinium (Gd), samarium (Sm) and holmium (Ho). Preferably, lanthanum is selected.

The supports may notably be a carbonaceous support (active coal, graphite, functionalized graphite or coal), metal oxides, for example titanium oxides or alumina. Preferably, the supports are stable supports under hydrothermal conditions.

Preferred catalysts comprising at least one lanthanide oxide are:
  MgLaO (mixed oxide based on magnesium and lanthanum), notably as described in J. Catalysis 2002 211, 150 or in Catalysis Today 152 (2010) 110-114 notably comprising MgO and La hydroxycarbonate;
  LaO (simple lanthanum oxide), either supported or not, notably supported, preferably on a carbonaceous support.

Because of their manufacturing processes, molecular sieves generally include organic molecules which were used for their synthesis. These organic molecules are called <<organic templates>> and the molecular sieves according to the invention may include organic templates. The organic template (notably CTA: cetyltrimethylammonium bromide) is indispensable for developing basicity of the sieves: the basic site is the oxygen of the lattice located in a position of a counter-anion of ammonium at the entrance of the pores.

Preferably, the catalysts of the molecular sieve type are molecular sieves based on silicon, notably those from the M41S family. Preferred catalysts of the molecular sieve type are those of the MCM48 and MCM50 type used in the presence of their organic template CTA, such as those described in Micropor. Mesopor. Mater. 70 (2004) 135.

Preferably, in the method of the present invention, the amount of catalyst is comprised between 0.5 and 100% by weight, preferably between 1 and 50% by weight, notably between 2 and 25% by weight, for example between 5 and 10% by weight, based on the weight of glucose.

Preferably, the amount of glucose is comprised between 0.5 and 15% by weight, preferably between 1 and 10% by weight, based on the weight of water.

The method of the present invention may be applied at a temperature comprised between 75 and 180° C., preferably between 80 and 150° C., for example between 85° C. and 100° C., notably at about 100° C. Advantageously, the method may therefore be applied at not very high temperatures, notably comprised between 85° C. and 100° C. This is notably made possible by the fact that the catalyst is resistant to poisoning by $CO_2$ and therefore has $CO_2$ adsorption reversibility at a low temperature. On the other hand, for catalysts which do not resist to $CO_2$ poisoning, the yield of the isomerisation will be very low or even zero at such temperatures.

The catalyst is applied in the absence of thermal activation in particular.

The method of the invention may also be applied at atmospheric pressure or under pressure of an inert gas, for example helium, up to a pressure of about 2 MPa (20 bars).

Advantageously, the catalyst may easily be recovered at the end of the reaction by any method known to one skilled in the art, notably by simple filtration. It is thus possible to recover the catalyst and to reuse it for a new isomerisation of glucose into fructose. In a particularly advantageous way, the catalyst may be reused as such, without any particular pretreatment, in 2, 3, 4 or even more reactions of isomerisation of glucose into fructose.

In a particular embodiment, the reaction may also be applied in the presence of water and of a solvent, notably an aprotic strongly polar solvent, for example DMSO (dimethylsulfoxide), DMF (dimethylformamide), NMP (N-methylpyrrolidone).

The solid basic catalyst may optionally undergo treatment before reaction with pyridine, generally with a strong base such as for example lutidine, ammonia, etc. Without intending to be bound to any theory, this treatment would give the possibility of blocking the possible Lewis acid sites of the catalyst. This treatment is therefore similar to poisoning of the catalyst. This treatment gives the possibility of improving the results in terms of conversion of glucose, fructose yield in and fructose selectivity. This treatment with pyridine notably gives the possibility of improving the fructose selectivity.

Advantageously, the method of the invention gives the possibility of obtaining the conversions of glucose of the order of between 20 and 50%, preferably of the order of 40, fructose yields of the order of 20 and 35%, preferably of the order of 32, and fructose selectivities of the order of 70 and 90%, preferably of the order of 80%.

Advantageously, the method of the invention gives the possibility of obtaining such results within a very short time. Notably, and surprisingly, the method of the invention may be conducted to its end, notably it gives the possibility of obtaining such conversion, yield and selectivity results in less than 5 hours, preferably in less than 2 hours, notably in about 1 hour, while the present enzymatic methods require more than 24 hours.

The catalytic system has the advantage, relatively to the other customary solid bases, of being applied in the absence of any notably thermal, pretreatment which is advantageous for an industrial application.

The invention also relates to a method for preparing HMF from glucose comprising the follow steps:
 i) isomerisation of glucose into fructose according to the method of the invention;
 ii) addition of a carboxylic acid to the reaction medium obtained in step i);
 iii) recovery of HMF.

The carboxylic acids of step ii) may be monoacids, diacids or triacids. They are notably selected from:
 acids of formula R—COOH wherein R represents a hydrogen atom or a linear or branched $C_1$-$C_5$, preferably $C_1$-$C_3$, alkyl chain, optionally substituted with one or several OH groups;
 acids of formula HOOC-L-COOH wherein L represents a bond or a linear or branched $C_1$-$C_5$, preferably $C_1$-$C_3$, alkyl chain, optionally substituted with one or several OH and/or COOH groups; or
 mixtures thereof.

Preferably, the carboxylic acid of step ii) is a monoacid selected from acids of formula R—COOH wherein R represents a hydrogen atom or a linear or branched $C_1$-$C_5$, preferably $C_1$-$C_3$, alkyl chain, optionally substituted with one or several OH groups.

Preferably, the carboxylic acid is formic acid, acetic acid, malic acid, citric acid, oxalic acid, lactic acid or mixtures thereof. Preferably, the carboxylic acid is formic acid, acetic acid, lactic acid or mixtures thereof. More preferably, the carboxylic acid is formic acid, acetic acid or a mixture thereof. Still most preferably, the carboxylic acid is acetic acid.

One skilled in the art, depending on whether he/she prefers promoting fructose conversion or HMF selectivity or having a good compromise between both of these features may determine the proportion and the nature of the acid to be integrated to the reaction medium. The amount of acid should not be too large with the risk of increasing the production of secondary by-products, notably humin. Thus, preferably the amount of acid is less than 80% by weight, generally comprised between 5 and 80% by weight, notably comprised between 10 and 60% by weight, for example about 50%, 20% or 10% by weight based on the weight of the liquid reaction medium.

Step (ii) may be conducted at a temperature comprised between 100 and 200° C., preferably between 120 and 180° C., for example between 150 and 180° C.

Step (ii) may also be applied at atmospheric pressure or under pressure of an inert gas, for example helium, up to a pressure of about 3.5 MPa (i.e. 35 bars).

Step (ii) may advantageously be applied in the presence of a heterogeneous acid catalyst. Preferably, the catalyst is selected from 12-tungstophosphoric acid, preferably dispersed on niobium hydroxide (NbOH); niobium hydroxide; zeolites such as H-ZSM-5 or H-Y, cationic clays of the K10 type, sulfonated coals; functionalized coals for example with carboxylic groups, for example subsequently to oxidation, for example oxidation by sodium hypochlorite; or mixtures thereof. Preferably, the catalyst is selected from 12-tungstophosphoric acid, preferably dispersed on niobium hydroxide (NbOH); niobium hydroxide; zeolites such as H-ZSM-5 or H-Y, cationic clays of the K10 type, sulfonated coals; functionalized coals, for example with carboxylic groups, or example subsequently to oxidation, for example oxidation by sodium hypochlorite or mixtures thereof. Preferably, the catalyst is selected from 12-tungstophosphoric acid, preferably dispersed on niobium hydroxide (NbOH); niobium hydroxide; sulfated zirconias; cesium acid salts of 12-tungstophosphoric acid ($Cs_2HPW_{12}O_{40}$); titanium dioxide; sulfonated coals; functionalized coals, for example with carboxylic groups, for example subsequently to oxidation, for example oxidation by sodium hypochlorite; or mixtures thereof. The addition of these catalysts notably gives the possibility of advantageously increasing the conversion into fructose, and the HMF selectivity. More preferably, the catalyst is a sulfonated coal or a functionalized coal.

When it is present, the amount of catalyst is preferably comprised between 2 and 100% by weight, preferably between 2 and 10% by weight, for example 5% by weight based on the initial glucose weight.

The present invention will now be described by means of non-limiting examples taken with reference to the drawing wherein.

Figure 1:
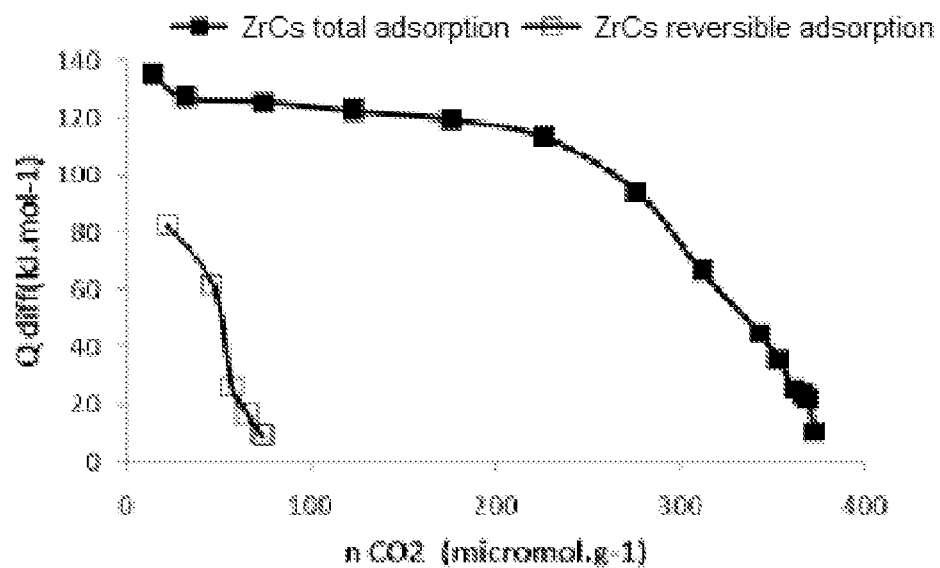
FIG. 1 illustrates the $CO_2$ adsorption calorimetric curves for a ZrC catalyst activated in vacuo at 450° C. for 2 hours, during the first so-called total adsorption (black squares), and then during the second so-called reversible adsorption (white squares).

EXAMPLE 1: ISOMERISATION OF GLUCOSE INTO FRUCTOSE IN THE PRESENCE OF VARIOUS SOLID BASIC CATALYSTS AT 100° C.

The reaction of isomerisation of glucose into fructose is achieved in a 100 ml autoclave by applying a solution of 1% by weight of glucose in water. The following amounts are introduced into the reactor: 30 g of distilled water, 0.3 g of glucose (1% by weight/water), 0.015 g of catalyst (5% by weight/glucose). No activation was applied to the solid catalysts. 20 bars of helium are introduced into the autoclave. The reaction medium is stirred by means of a magnetic stirrer. The reaction medium is brought to the reaction temperature by means of electric resistors regulated to 100° C. After 2 hours of reaction at 100° C., the autoclave is cooled by means of an ice bath. The conversion of glucose and the fructose molar yield are determined by HPLC-RID analysis (column: COREGEL 87C).

The isomerisation was achieved in the presence of various catalysts, i.e.:
a) catalysts according to the invention:
   MgLaO;
   MgLaO treated with pyridine;
   MCM48;
   MCM50.
b) catalysts of the prior art:
   Sn Beta;
   ZrCs;
   NaOH (in this particular case the reaction was conducted at 50° C.).

The isomerisation was also achieved according to the procedure above in the absence of any catalyst.

| Catalyst | Conversion (%) | Fructose yld (%) | Mannose yld (%) | Others: yld (%) |
|---|---|---|---|---|
| MgLaO | 52.6 | 28.2 | 5.1 | 6.5 |
| MgLaO treated with Pyridine | 28.2 | 22.1 | 2.1 | 2.6 |
| MCM48 | 22 | 17.5 | 2 | 2 |
| MCM50 | 16.4 | 13.6 | 0.8 | 0.4 |
| SnBeta | 2 | 1.8 | 0.2 | |
| ZrCs | 3.5 | 2.5 | 1 | 0 |
| enzyme, (comparative*) | | 43 | | |
| NaOH, 50° C. | 45 | 32 | 4 | 6 |
| Without any catalyst | 0.6 | 0.4 | 0 | 0 | yld = molar yield
*results reported in Dahai Yu et al. Process Biochemistry 46 (2011) 599-603

The results show that the catalysts according to the invention have improved activity (notably in terms of conversion of glucose, fructose yield and fructose selectivity) as compared with the basic solid catalysts of the state of the art, not having any $CO_2$ adsorption reversibility, such as for example ZrCs or as compared with an Sn-Beta Lewis acid. The results also show that the application of the method according to the invention gives the possibility of obtaining better results or similar results as compared with the enzymatic method or with the methods by catalysis with homogeneous bases.

Finally, the results show that the treatment of the catalyst with pyridine gives the possibility of improving fructose selectivity.

EXAMPLE 2: ISOMERISATION OF GLUCOSE INTO FRUCTOSE IN THE PRESENCE OF VARIOUS SOLID BASIC CATALYSTS AT 100° C.

The reaction of isomerisation of glucose into fructose is achieved in a 100 ml autoclave by applying a 2% by weight solution of glucose in water. The following amounts are introduced into the reactor: 30 g of distilled water, 0.6 g of glucose (2% by weight/water), 0.030 g of catalyst (5% by weight/glucose). No activation was applied to the solid catalysts. 20 bars of helium are introduced into the autoclave. The reaction medium is stirred by means of a magnetic stirrer. The reaction medium is brought to the reaction temperature by means of electric resistors regulated to 100° C. After 2 hours or 1 hour** of reaction at 100° C., the autoclave is cooled by means of an ice bath. The conversion of glucose and the fructose molar yield are determined by HPLC-RID analysis (column: COREGEL 87C).

The isomerisation was achieved in the presence of various catalysts, i.e.:
   MgLaO (mixed oxide based on magnesium and lanthanum) (for 1 hour and 2 hours);
   LaO (simple lanthanum oxide/coal) (LaOH/C);
   ZrCs (comparative);
   hydrotalcite (Mg/Al=3) for 1 hour. (comparative)

| Catalyst | Conversion (%) | Fructose yld (%) | Mannose yld (%) | Others: yld (%) |
|---|---|---|---|---|
| 5% MgLaO | 35.61 | 25.57 | 4.05 | 3.32 |
| 5% LaOH/C | 51.72 | 25.97 | 6.95 | 5.68 |
| 5% ZrCs | 5.14 | 4.96 | 0.39 | 0 |
| 5% MgLaO** | 34.54 | 27.36 | 3.54 | 4.14 |
| 5% HDT Mg/Al = 3** | 24.64 | 15.54 | 1.09 | 0 | yld = molar yield,
**= reaction time 1 hour

The results show that the catalysts according to the invention have improved activity (notably in terms of conversion of glucose, fructose yield and fructose selectivity) as compared with solid catalysts of the state of the art, not having any $CO_2$ adsorption reversibility (for example ZrCs). The isomerisation applied according to the method of the invention gives the possibility of obtaining improved results in terms of conversion into fructose and fructose selectivity as compared with the method applied in the presence of hydrotalcite Mg/Al.

EXAMPLE 3: ISOMERISATION OF GLUCOSE INTO FRUCTOSE IN THE PRESENCE OF VARIOUS SOLID BASIC CATALYSTS AT 150° C.

The reaction of isomerisation with glucose into fructose is achieved in a 100 ml autoclave by applying a solution of 1% by weight glucose in water. The following amounts are introduced into the reactor: 30 g of distilled water, 0.3 g of glucose (1% by weight/water), 0.015 g of catalyst (5% by weight/glucose). No activation was applied to the solid catalysts. 20 bars of helium are introduced into the autoclave. The reaction medium is stirred by means of a magnetic stirrer. The reaction medium is brought to the reaction temperature by means of electric resistors regulated to 150° C. After 2 hours of reaction at 150° C., the autoclave is cooled by means of an ice bath. The conversion of glucose and the fructose molar yield are determined by HPLC-RID analysis (column: COREGEL 87C).

The isomerisation was achieved in the presence of various catalysts, i.e.:
MgLaO;
Sn-Beta (comparative);
ZrCs treated in vacuo (i.v.) at 450° C. for 2 hours, this treatment being usually carried out for activating the catalyst (comparative);
ZrCs (comparative).

The isomerisation was also achieved according to the procedure above in the absence of catalysts.

| Catalyst | Conversion (%) | Fructose yld (%) | Mannose yld (%) | Others: yld (%) |
|---|---|---|---|---|
| 5% MgLaO | 59.4 | 23.0 | 6.9 | 5.1 |
| 5% Sn-Beta | 15.8 | 9.9 | 1.4 | 1.2 |
| 5% ZrCs treated i.v. at 400° C./2 h | 14.4 | 8.4 | 1.6 | 1.2 |
| Without any catalyst | 7.2 | 3.5 | 0.5 | 2.3 |
| 5% ZrCs | 13.3 | 5.8 | 2.9 | 2.4 | yld = molar yield

The results show that the ZrCs catalyst, characterized by irreversible $CO_2$ adsorption at 30° C. and by the presence of strong basic sites in particular after activation in vacuo at 450° C. is more active at 150° C. than at 100° C. but remains substantially less active than MgLaO, a catalyst according to the invention. The results show that the pretreatment of ZrCs does not give the possibility of improving the activity of the catalyst. The results also show that the Sn-Beta catalyst, which is a Lewis acid, is more active at 150° C. than at 100° C. but remains substantially less active than MgLaO, a catalyst according to the invention.

EXAMPLE 4: ISOMERISATION OF GLUCOSE INTO FRUCTOSE, COMPARISON OF MGLAO WITH ALUMINATE AT 100° C.

The reaction of isomerisation of glucose into fructose is achieved in a 100 ml autoclave by applying a 2% by weight glucose solution in water. The following amounts are introduced into the reactor: 30 g of distilled water, 0.6 g of glucose (2% by weight/water), 0.060 g of catalyst (10% by weight/glucose). No activation was applied to the solid catalysts. 20 bars of helium are introduced into the autoclave. The reaction medium is stirred by means of a magnetic stirrer. The reaction medium is brought to the reaction temperature by means of electric resistors regulated to 100° C. After 1 hour of reaction at 100° C., the autoclave is cooled by means of an ice bath. The conversion of glucose and the fructose molar yield are determined by HPLC-RID analysis (column: COREGEL 87C).

Isomerisation was achieved in the presence of 10% of MgLaO by weight based on the glucose weight and of 10% of sodium aluminate (comparative) by weight based on the glucose weight.

| catalyst | Conversion (%) | Fructose yld (%) | Others: yld (%) |
|---|---|---|---|
| 10% MgLaO | 38.7 | 31.2 | 8.6 |
| 10% sodium aluminate | 61.4 | 28.4 | 17.0 | yld = molar yield

The results show that with MgLaO in the method of the invention, it is possible to limit the formation of by-products. Indeed, although the conversion of glucose is lower in the method of the invention than in the method catalyzed by sodium aluminates, the fructose yield and the fructose selectivity are higher therein.

EXAMPLE 5: ISOMERISATION OF GLUCOSE INTO FRUCTOSE CATALYZED BY MGLAO, INFLUENCE OF TEMPERATURE

The reaction of isomerisation of glucose into fructose is achieved in a 100 ml autoclave by applying a solution of 1% by weight of glucose in water. The following amounts are introduced into the reactor: 30 g of distilled water, 0.3 g of glucose (1% by weight/water), 0.015 g of catalyst (5% by weight/glucose). No activation was applied to the solid catalyst. 20 bars of helium are introduced into the autoclave. The reaction is stirred by means of a magnetic stirrer. The reaction medium is brought to the reaction temperature by means of electric resistors regulated to the reaction temperature. After 2 hours of reaction at the reaction temperature, the autoclave is cooled by means of an ice bath. The conversion of glucose and the fructose molar yield are determined by HPLC-RID analysis (column: COREGEL 87C).

The isomerisation was achieved in the presence of 5% by weight of MgLaO based on the glucose weight at 85° C. (for 13 hours), 100° C., 150° C. and 180° C.

| Temperature | Conversion (%) | Fructose yld (%) | Others: yld (%) |
|---|---|---|---|
| 85° C.** | 37.5 | 26.6 | 6.8 |
| 100° C. | 52.6 | 28.2 | 11.6 |
| 150° C. | 59.4 | 23.0 | 12.1 |
| 180° C. | 78.0 | 8.1 | 28.2 | yld = molar yield,
**13 hours

The results show that the more the temperature increases, the more the conversion of glucose is significant. However, this increase in the temperature is also expressed by an increase in the occurrence of by-products and therefore by a decrease in the fructose yield and therefore in the fructose selectivity.

Thus, the best compromise in terms of conversion of glucose, fructose yield and selectivity is obtained for temperatures below 150° C. and notably below 100° C.

EXAMPLE 6: ISOMERISATION OF GLUCOSE INTO FRUCTOSE CATALYZED BY MGLAO, INFLUENCE OF THE GLUCOSE CONCENTRATION

The reaction of isomerisation of glucose into fructose is achieved in a 100 ml autoclave by applying a solution with different percentages by weight of glucose in water. The following amounts are introduced into the reactor: 30 g of distilled water, 0.3 g of glucose (1% by weight/water) or 0.6 g of glucose (2% by weight/water) or 1.5 g of glucose (5% by weight/water) or 3 g of glucose (10% by weight/water), 5% by weight of catalyst/glucose. No activation was applied to the solid catalyst. 20 bars of helium are introduced into the autoclave. The reaction medium is stirred by means of a magnetic stirrer. The reaction medium is brought to 100° C. by means of electric resistors regulated to 100° C. After 2 hours of reaction at 100° C., the autoclave is cooled by means of an ice bath. The conversion of glucose and the fructose molar yield are determined by HPLC-RID analysis (column: COREGEL 87C).

The isomerisation was achieved in the presence of 1%, 2%, 5% and 10% by weight of glucose based on the weight of water.

|  | Conversion | Fructose yld (%) | Others: yld (%) |
|---|---|---|---|
| 1% Glucose | 52.6 | 28.2 | 11.6 |
| 2% Glucose | 35.6 | 25.6 | 7.4 |
| 5% Glucose | 47.3 | 28.6 | 11.5 |
| 10% Glucose | 47.9 | 29.1 | 13.2 | yld = molar yield

The results show that the glucose concentration in the reaction medium does not significantly modify the results in terms of conversion of glucose, fructose yield and selectivity.

EXAMPLE 7: ISOMERISATION OF GLUCOSE INTO FRUCTOSE, CATALYZED BY MGLAO, INFLUENCE OF THE CATALYST MASS

The reaction of isomerisation of glucose into fructose is achieved in a 100 ml autoclave by applying a solution of 2% by weight of glucose in water. The following amounts are introduced into the reactor: 30 g of distilled water, 0.6 g of glucose (2% by weight/water) 0.03 g of catalyst (5% by weight/glucose) or 0.6 g of catalyst (10% by weight/glucose) or 0.12 g of catalyst (20% by weight/glucose) or 0.3 g of catalyst (50% by weight/glucose) or 0.6 g of catalyst (100% by weight/glucose). No activation was applied to the solid catalyst. 20 bars of helium are introduced into the autoclave. The reaction medium is stirred by means of a magnetic stirrer. The reaction medium is brought to the reaction temperature by means of electric resistors regulated to 100° C. After 1 hour of reaction at 100° C., the autoclave is cooled by means of an ice bath. The conversion of glucose and the fructose molar yield are determined by HPLC-RID analysis (column: COREGEL 87C).

Isomerisation is achieved in the presence of 5%, 10%, 20%, 50% and 100% by weight of MgLaO based on the glucose weight.

|  | Conversion (%) | Fructose yld (%) | Others: yld (%) |
|---|---|---|---|
| 5% MgLaO | 34.5 | 27.4 | 7.7 |
| 10% MgLaO | 38.7 | 31.2 | 8.6 |
| 20% MgLaO | 43.7 | 28.4 | 10.6 |
| 50% MgLaO | 56.2 | 29.0 | 18.9 |
| 100% MgLaO | 60.8 | 26.0 | 20.6 | yld = molar yield

The results show that an increase in the catalyst mass relatively to glucose gives the possibility of increasing the conversion of glucose. However, the fructose yield and selectivity decrease. The best compromise between conversion of glucose and fructose selectivity is obtained for catalyst amounts of less than 20% by weight based on the glucose weight.

EXAMPLE 8: RESISTANCE OF MGLAO TO POISONING BY $CO_2$

The reaction of isomerisation of glucose into fructose is achieved in a 100 ml autoclave by applying a solution of 2% by weight of glucose in water. The following amounts are introduced into the reactor: 30 g of distilled water, 0.6 g of glucose (2% by weight/water) 0.03 g of catalyst (5% by weight/glucose). The catalyst was used without any activation or after the following activation steps: 0.03 g of catalyst are treated in a secondary vacuum at 400° C. for 2 hours, and then rapidly introduced into the reaction medium without putting them back in air. Another step for activation of this catalyst also consisted of putting the catalyst in contact with 10 torrs of $CO_2$, subsequent to the treatment in a secondary vacuum at 400° C. for 2 hours. The reaction medium is stirred by means of a magnetic stirrer. The reaction medium is brought to the reaction temperature by means of electric resistors regulated to 100° C. After 1 hour of reaction at 100° C., the autoclave is cooled by means of an ice bath. The conversion of glucose and the fructose molar yield are determined by HPLC-RID analysis (column: COREGEL 87C).

Isomerisation was achieved with non-treated MgLaO, with MgLaO treated at 400° C. in vacuo for 2 hours, and with MgLaO treated at 400° C. in vacuo for 2 hours, and then under 10 torrs of $CO_2$. Usually, with the treatment at 400° C. in vacuo, it is possible to activate a catalyst.

|  | Conversion (%) | Fructose yld (%) | Others: yld (%) |
|---|---|---|---|
| 5% MgLaO treated at 400° C. i.v.//2 h | 31.7 | 23.5 | 6.5 |
| MgLaO | 35.8 | 25.4 | 6.5 |
| 5% MgLaO treated at 400° C. i.v.//2 h + $CO_2$ | 33.1 | 24.9 | 6.3 | yld = molar yield, i.v.//2 h = treatment in vacuo for 2 hours

The results do not show any significant difference in terms of conversion of glucose, fructose yield and selectivity, depending on whether the MgLaO was either treated or not and was put into contact with $CO_2$. These results show therefore that MgLaO is resistant to poisoning by $CO_2$.

EXAMPLE 9: KINETICS OF THE REACTION CATALYZED BY MGLAO AND MCM50

The reaction of isomerisation of glucose into fructose is achieved in a 100 ml autoclave by applying a solution of 1% or 2% by weight of glucose in water. The following amounts are introduced into the reactor: 30 g of distilled water, 0.3 g of glucose (1% by weight/water) or 0.6 g of glucose (2% by weight/water), 5% or 20% by weight of catalyst based on glucose. The catalyst was used without activation. The reaction medium is stirred by means of a magnetic stirrer. The reaction medium is brought to the reaction temperature by means of electric resistors regulated to 100° C. The reaction medium is regularly sampled in order to determine the time-dependent changes in the conversion of glucose and in the fructose yield during the reaction. After 2 hours of reaction at 100° C., the autoclave is cooled by means of an ice bath. The conversion of glucose and the fructose molar yield are determined by HPLC-RID analysis (column: COREGEL 87C).

The isomerisation was achieved with 5% by weight of MgLaO based on the weight of glucose and with 20% by weight of MgLaO based on the weight of glucose and with 5% by weight of [CTA]Si-MCM50 based on the weight of glucose, at 100° C.

|  | Conversion (%) | Fructose yld (%) | Mannose yld (%) | Others: yld (%) |
|---|---|---|---|---|
| 5% MgLaO | 8.2 (5 mins) | 7.3 | 0.3 | 0 |
| 5% MgLaO | 20.2 (15 mins) | 18.2 | 1.4 | 1.1 |
| 5% MgLaO | 25.9 (30 mins) | 21.0 | 2.0 | 1.5 |
| 5% MgLaO | 34.5 (60 mins) | 27.4 | 3.5 | 4.1 |
| 5% MgLaO | 35.6 (120 mins) | 25.6 | 4.0 | 3.3 | yld = molar yield; 2% by weight of glucose/water

|  | Conversion (%) | Fructose yld (%) | Mannose yld (%) | Others: yld (%) |
|---|---|---|---|---|
| 20% MgLaO | 43.7 (60 mins) | 28.4 | 4.4 | 6.2 |
| 20% MgLaO | 55.8 (120 mins) | 26.9 | 4.8 | 7.1 | yld = molar yield; 2% by weight of glucose/water

|  | Conversion (%) | Fructose yld (%) | Mannose yld (%) | Others: yld (%) |
|---|---|---|---|---|
| 5% MCM50 | 9.8 (30 mins) | 8.8 | 0.5 | 0.16 |
| 5% MCM50 | 14.2 (60 mins) | 12.1 | 0.6 | 0.5 |
| 5% MCM50 | 17.6 (90 mins) | 15.4 | 0.9 | 0.9 |
| 5% MCM50 | 21.6 (120 mins) | 16.0 | 1.1 | 1.1 | yld = molar yield; 1% in weight by weight of glucose in water

The results show that by increasing the reaction time, it is possible to increase the conversion of glucose which is however accomplished to the detriment of selectivity. The results show that after one hour of reaction, good fructose yields are obtained which are quasi equivalent to what may be obtained with the enzymatic method.

EXAMPLE 10: RECYCLING OF THE CATALYST

The reaction of isomerisation of glucose into fructose is achieved in a 100 ml autoclave by applying a solution of 2% by weight of glucose in water. The following amounts are introduced into the reactor: 30 g of distilled water, 0.6 g of glucose (2% by weight/water), and 0.030 g of catalyst (5% by weight/glucose). No activation was applied to the solid catalyst. 20 bars of helium are introduced into the autoclave. The reaction medium is stirred by means of a magnetic stirrer. The reaction medium is brought to the reaction temperature by means of electric resistors regulated to 100° C. After 1 hour of reaction at 100° C., the autoclave is cooled by means of an ice bath; the catalyst is separated by filtration so as to be reused. The catalyst is reintroduced into the autoclave without any particular treatment, the following amounts are again introduced into the autoclave: 30 g of distilled water, 0.6 g of glucose (2% by weight/water). 3 cycles of recycling tests of the catalyst were carried out in an identical way. The conversion of glucose and the fructose molar yield are determined by HPLC-RID (column: CORE-GEL 87C).

|  | Conversion (%) | Fructose yld (%) | Others: yld (%) |
|---|---|---|---|
| $1^{st}$ use | 38.7 | 31.2 | 8.6 |
| $2^{nd}$ use | 27.6 | 22.4 | 4.7 |
| $3^{rd}$ use | 30.3 | 23.4 | 5.2 |
| $4^{th}$ use | 29.8 | 23.5 | 5.2 | yld = molar yield

The results show that the catalyst may be reused for several isomerisations without any preliminary treatment. No incidence on the conversion of glucose, on the fructose yield and selectivity is observed even after 4 uses of the catalyst without any treatment.

EXAMPLE 11: ISOMERISATION IN THE PRESENCE OF A SOLVENT

The reaction of isomerisation of glucose into fructose is achieved in a 100 ml autoclave by applying a solution of 1% by glucose in water. The following amounts are introduced into the reactor: 15 g of distilled water, 15 g of DMSO, 0.3 g of glucose (1% by weight/water+DMSO), 0.015 g of catalyst (5% by weight/glucose) or 0.03 g of catalyst (10% by weight/water). No activation was applied to the solid catalysts. 20 bars of helium are introduced into the autoclave. The reaction medium is stirred by means of a magnetic stirrer. The reaction medium is brought to the reaction temperature by means of electric resistors regulated to 100° C. After 1 hour or 2 hours or 14 hours of reaction at 100° C., the autoclave is cooled by means of an ice bath. The conversion of glucose and the fructose molar yield are determined by HPLC-RID (column: COREGEL 87C).

The reaction of isomerisation was carried out with different amounts of catalyst in a reaction medium of water+DMSO:
  5% by weight of MgLaO based on the glucose weight, with 50% by weight of DMSO based on the total weight of the water+DMSO medium;
  10% by weight of MgLaO based on the glucose weight, with 50% by weight of DMSO based on the total weight of the water+DMSO medium;

5% by weight of MgLaO based on the glucose weight, with 50% by weight of DMSO based on the total weight of the water+DMSO medium for 14 hours.

|  | Conversion (%) | Fructose yld (%) | Mannose yld (%) | Others: yld (%) |
|---|---|---|---|---|
| 5% MgLaO, 50% DMSO 1 hour reaction | 13.2 | 12.1 | 0.7 | 0 |
| 10% MgLaO, 50% DMSO 2 hour reaction | 23.9 | 19.1 | 2.5 | 0.7 |
| 5% MgLaO, 50% DMSO 14 hour reaction | 31.6 | 26.1 | 3.7 | 0 | yld = molar yield

The results show that the reaction may be conducted in a not completely aqueous solvent, i.e. in the presence of an organic solvent.

EXAMPLE 12: VARIATION OF THE CATALYST

The reaction of isomerisation of glucose into fructose is achieved in a 100 ml autoclave by applying a solution of 2% by weight of glucose in water. The following amounts are introduced into the reactor: 30 g of distilled water, 0.6 g of glucose (2% by weight/water), 5% or 10% by weight of catalyst based on the glucose weight. No activation was applied to the solid catalysts. 20 bars of helium are introduced into the autoclave. The reaction medium is stirred by means of a magnetic stirrer. The reaction medium is brought to the reaction temperature by means of electric resistors regulated to 100° C. After 1 hour of reaction at 100° C., the autoclave is cooled by means of an ice bath. The conversion of glucose and the fructose molar yield are determined by HPLC-RID analysis (column: COREGEL 87C).

The isomerisation was achieved in the presence of different catalysts, i.e.:
  MgLaO (mixed oxide based on magnesium and lanthanum)
  CeMgO (mixed oxide based on magnesium and cerium)
  HY (a zeolite no longer comprising any organic template): comparative example
  ZSM5 (a zeolite no longer comprising any organic template): comparative example

| Catalyst | Conversion | Fructose yld | Others: yld |
|---|---|---|---|
| LaMgO * | 38.67 | 31.24 | 8.6 |
| LaMgO | 34.54 | 27.36 | 7.68 |
| CeMgO | 27.44 | 20.35 | 3.64 |
| HY | 7.32 | 2.32 | 0 |
| ZSM5 | 3.05 | 1.06 | 0.48 | yld = molar yield, 2% glucose, 1 hour, 100° C., 5% catalyst,
* 10% catalyst

These results show that it is possible to apply the method of the invention with various lanthanides while obtaining good results in terms of conversion and fructose yield.

EXAMPLE 13: HMF PREPARATION FROM GLUCOSE

The reaction of conversion of glucose into HMF is achieved by integrating two steps in a single autoclave: a first step for isomerisation of glucose into fructose in the presence of MgLaO at 100° C. (or at 150° C.) in a 100% water medium for 2 hours, followed by a second step for dehydrating fructose into HMF in the presence of carboxylic acids. The synthesis of HMF is carried out in a 100 ml autoclave by applying a solution of 1% by weight of glucose in water. The following amounts are introduced into the reactor: 15 g of distilled water, 0.3 g of glucose (2% by weight/water), 0.015 g of catalyst (5% by weight/glucose). No activation was applied to the catalyst MgLaO. 20 bars of helium are introduced into the autoclave. The reaction medium is stirred by means of a magnetic stirrer. The reaction medium is brought to the reaction temperature by means of electric resistors regulated to 100° C. for 2 hours (or to 150° C. for 1.5 hours). The second step then begins by adding 15 g of acetic acid to the reaction medium. The reaction is continued for 2 hours at 150° C. At the end of the reaction, the autoclave is cooled by means of an ice bath. The conversion of glucose and the fructose molar yield are determined by HPLC-RID analysis (column: COREGEL 87C).

|  | Conversion (%) | HMF yld (%) | Fructose yld (%) | Mannose yld (%) | Others: yld (%) |
|---|---|---|---|---|---|
| Step 1: MgLaO-100% water-150° C.-1 h 30 mins Step 2: 50% acetic acid/50% water-150° C.-2 hours | 56.5 | 16.8 | 3.1 | 6.2 | 2.4 |
| Step 1: MgLaO-100% water-100° C.-2 hours Step 2: 50% acetic acid/50% water-150° C.-2 hours | 33.5 | 15.4 | 1.1 | 1.3 | 2.1 | yld = molar yield

The results show that the method according to the invention gives the possibility of preparing a HMF from glucose with a suitable yield.

EXAMPLE 14: STUDY OF THE $CO_2$ ADSORPTION REVERSIBILITY

The reversibility of the $CO_2$ adsorption by a catalyst may be determined by measurements of $CO_2$ (total and reversible) adsorption isotherms by volumetric measurement coupled with calorimetry. The $CO_2$ adsorption measurements are conducted by means of a calorimetry Tian Calvet, they are coupled with measurements of $CO_2$ adsorption isotherms by means of volumetric equipment in Pyrex equipped with a precision pressure gauge. The solid is introduced into the cell of the calorimeter held at the measurement temperature (30° C.) so as to be pretreated in vacuo at this temperature until a good vacuum is obtained ($10^{-5}$ torrs). The $CO_2$ is introduced in small increments at 30° C., the released heat is measured at each dose of $CO_2$ as well as the equilibrium pressure. The adsorption isotherm is determined up to the equilibrium pressure of 1 torr. After the measurement of the first isotherm (total adsorption) conducted in parallel with the first calorimetric curve, a second isotherm is produced (reversible adsorption) and in parallel with the second calorimetric curve after having treated in vacuo the solid catalyst at 30° C. for 15 hours. The conclusion is drawn that $CO_2$ adsorption is reversible when it is observed that the isotherms (both total and reversible) may be superposed and that the (total and reversible) calorimetric curves may be superposed upon accepting a deviation of less than 20%.

The results obtained for the ZrCs (comparative), MCM-48, MCM-50 catalysts are shown in FIGS. 1 to 4.

FIG. 1 represents the calorimetric curves of $CO_2$ adsorption for a ZrCs catalyst activated in vacuo at 450° C. for 2 hours. The black squares show the time-dependent change in the $CO_2$ adsorption differential heat, with $CO_2$ recovery during the first adsorption (total adsorption), the white squares show the time-dependent change in the $CO_2$ adsorption differential heats with $CO_2$ recovery during the second adsorption (reversible adsorption), i.e. achieved after a treatment in vacuo of the catalyst at 30° C. for 15 hours subsequent to the first $CO_2$ adsorption. It is noted that zirconia doped with Cs, ZrCs, activated in vacuo at 450° C., has strong basic sites, characterized by a homogeneous distribution in force and by a $CO_2$ adsorption differential heat of the order of 125-130 kJ·mol$^{-1}$. The second calorimetric curve obtained after a first adsorption of $CO_2$ followed by a treatment in vacuo at 30° C. for 15 hours, shows the non-reversibility of $CO_2$ adsorption on ZrCs activated at 450° C. in vacuo. The second calorimetric curve is characterized by an initial $CO_2$ adsorption differential heat of 80 kJ·mol$^{-1}$ which rapidly decreases with $CO_2$ recovery. Both calorimetric curves cannot be superposed, this showed the non-reversibility of $CO_2$ adsorption of ZrCs activated at 450° C.

Figure 2:
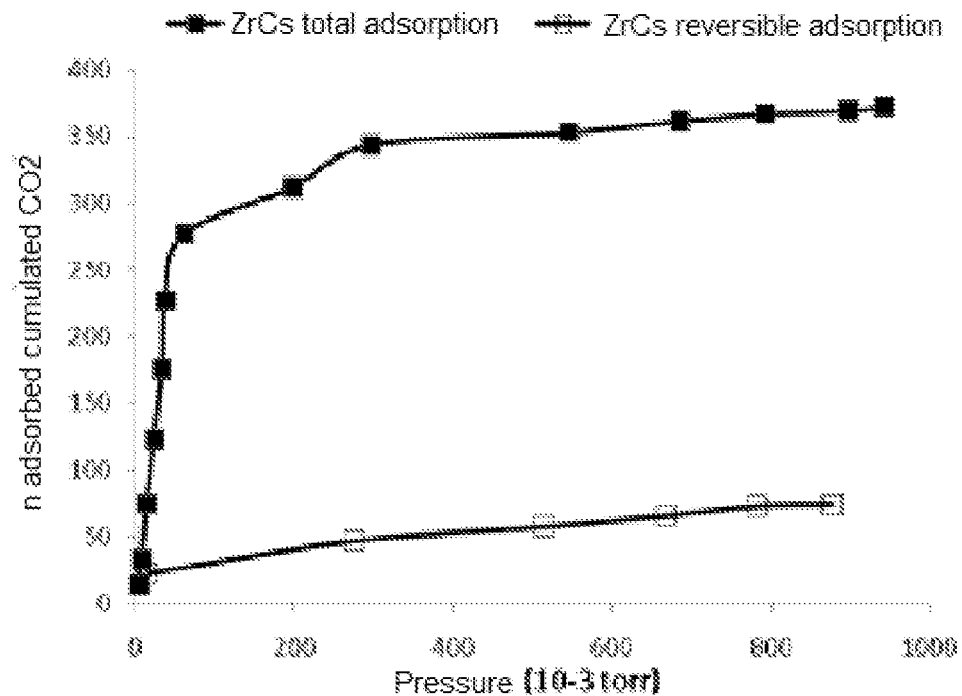
FIG. 2 shows the $CO_2$ adsorption isotherms measured in parallel with the measurement of the $CO_2$ adsorption differential heats with $CO_2$ recovery during the first and the second adsorption of $CO_2$ (total and reversible adsorptions respectively).

FIG. 2 shows the $CO_2$ adsorption isotherms measured in parallel with the measurement of the $CO_2$ adsorption differential heats with $CO_2$ recovery during the first and the second adsorption of $CO_2$ (total and reversible adsorptions, respectively). These curves show the non-reversibility of $CO_2$ adsorption on activated ZrCs in vacuo at 450° C.: while total adsorption corresponds to an adsorption of 350 micromol·g$^{-1}$ of $CO_2$, the reversible adsorption is limited to 50 micromol·g$^{-1}$ of $CO_2$. This shows that both isotherms do not superpose each other on activated ZrCs at 450° C. in vacuo, the adsorption of $CO_2$ on ZrCs activated at 450° C. is non-reversible.

Figure 3:
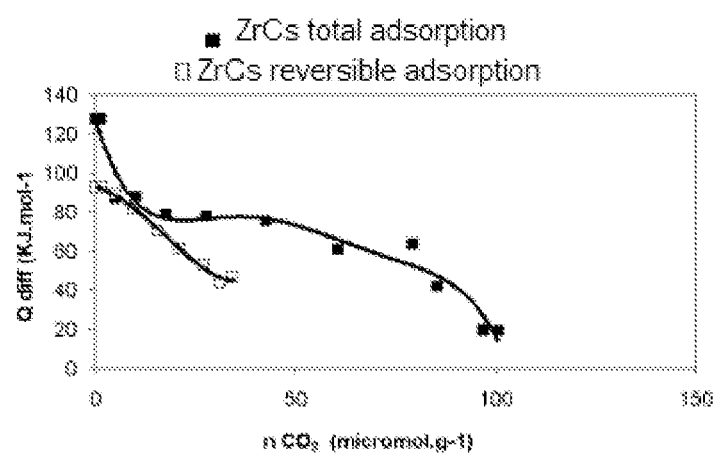
FIG. 3 illustrates the $CO_2$ adsorption calorimetric curves for a ZrC catalyst pretreated in vacuo at 30° C. for 24 hours, during the first so-called total adsorption (black squares), and then during the second so-called reversible adsorption (white squares).

FIG. 3 represents the $CO_2$ adsorption calorimetric curves for a ZrCs catalyst pretreated in vacuo at 30° C. for 24 hours. The black squares show the time-dependent change in the $CO_2$ adsorption differential heat with $CO_2$ recovery during the first adsorption (total adsorption), the white squares show the time-dependent change in the $CO_2$ adsorption differential heats with recovery of $CO_2$ during the second adsorption (reversible adsorption) i.e. achieved after a treatment in vacuo of the catalyst at 30° C. for 15 hours subsequent to the first $CO_2$ adsorption. It is noted that zirconia doped with Cs, ZrCs, activated in vacuo at 30° C. has a few strong basic sites, characterized by a $CO_2$ adsorption differential heat of the order of 125-130 kJ·mol$^{-1}$ and a majority of weaker basic sites showing a $CO_2$ adsorption differential heat of the order of 80 kJ·mol$^{-1}$. A comparison with the second calorimetric curve obtained after a first $CO_2$ adsorption followed by a treatment in vacuo at 30° C. for 15 hours shows the non-reversibility of $CO_2$ adsorption on ZrCs activated at 30° C. in vacuo. The second calorimetric curve is characterized by an initial $CO_2$ adsorption differential heat of 90 kJ·mol$^{-1}$, which rapidly decreases with recovery of $CO_2$. Both calorimetric curves cannot be superposed, this shows the non-reversibility of $CO_2$ adsorption on ZrCs activated in vacuo at 30° C. for 24 hours.

Figure 4:
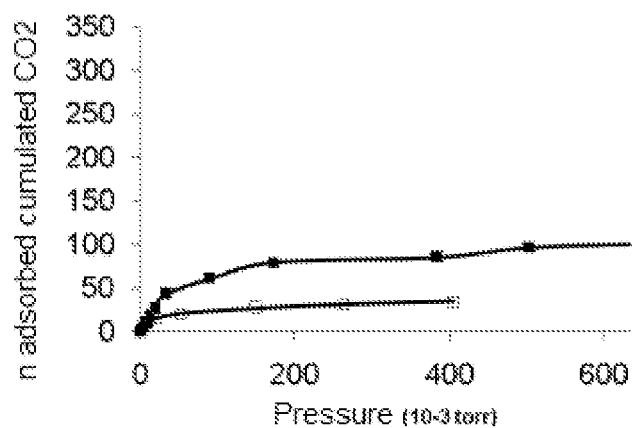
FIG. 4 shows the $CO_2$ adsorption isotherms measured in parallel with the measurement of the $CO_2$ adsorption differential heats with $CO_2$ recovery during the first and second adsorption of $CO_2$ (total and reversible adsorptions respectively).

FIG. 4 shows the $CO_2$ adsorption isotherms measured in parallel with the measurement of the $CO_2$ adsorption differential heats with recovery of $CO_2$ during the first and second adsorption of $CO_2$ (total and reversible adsorptions respectively). These curves show the non-reversibility of $CO_2$ adsorption on ZrCs pretreated in vacuo at 30° C.: while total adsorption corresponds to an adsorption of 100 micromol·g$^{-1}$ of $CO_2$, the reversible adsorption is limited to 25 micromol·g$^{-1}$ of $CO_2$ showing that both isotherms do not superpose each other on ZrCs pretreated at 30° C. in vacuo for 24 hours.

Figure 5:
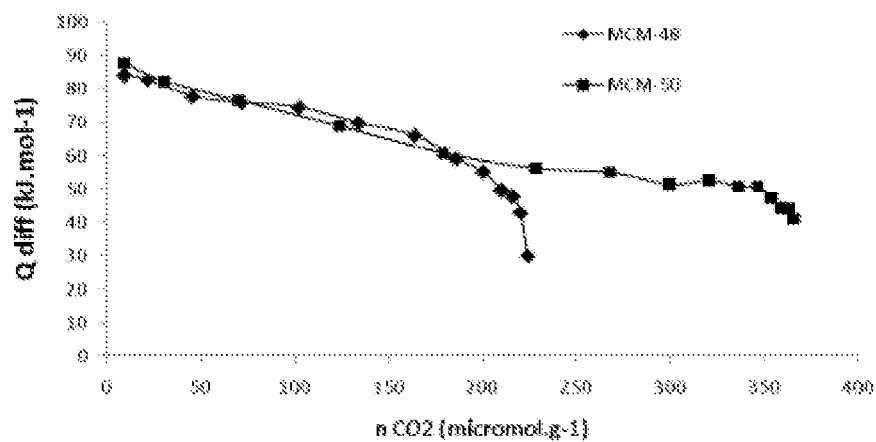
FIG. 5 illustrates the $CO_2$ adsorption calorimetric curves (first total adsorption) for [CTA]Si-MCM48, and [CTA]Si-MCM50 catalysts.

FIG. 5 represents the $CO_2$ adsorption calorimetric curves (first total adsorption) for [CTA]Si-MCM48, and [CTA]Si-MCM50 catalysts.

Figure 6:
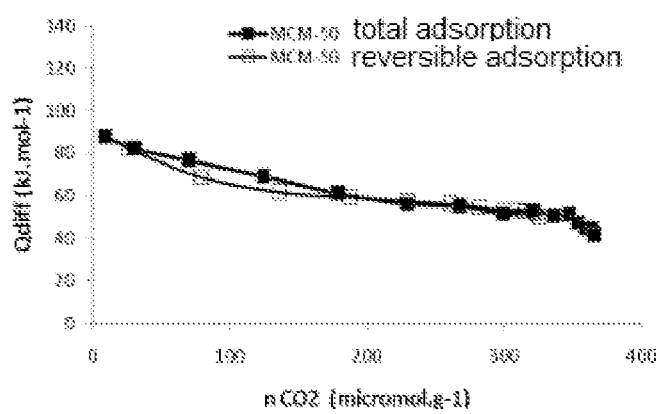
FIG. 6 illustrates the $CO_2$ adsorption calorimetric curves for a [CTA]Si-MCM50 catalyst pretreated in vacuo at 30° C. for 24 hours, during the first so-called total adsorption (black squares), and then during the second so-called reversible adsorption (white squares).

FIG. 6 represents the $CO_2$ adsorption calorimetric curves for a [CTA]Si-MCM50 catalyst pretreated in vacuo at 30° C. for 24 hours. The black squares show the time-dependent change in the $CO_2$ adsorption differential heat with $CO_2$ recovery during the first adsorption (total adsorption), the white squares show the time-dependent change in the $CO_2$ adsorption differential heats with $CO_2$ recovery during the second adsorption (reversible adsorption), i.e. achieved after a treatment in vacuo of the catalyst at 30° C. for 15 hours subsequent to the first $CO_2$ adsorption. It is noted that the catalyst [CTA]Si-MCM50, activated in vacuo at 30° C. for 24 hours, has weak basic sites, characterized by a $CO_2$ adsorption differential heat of the order of 75-80 kJ·mol$^{-1}$. The second calorimetric curve (reversible adsorption) obtained after a first $CO_2$ adsorption followed by treatment in vacuo at 30° C. for 15 hours is quasi-similar to the first calorimetric curve (total adsorption). Both calorimetric curves may be superposed.

Figure 7:
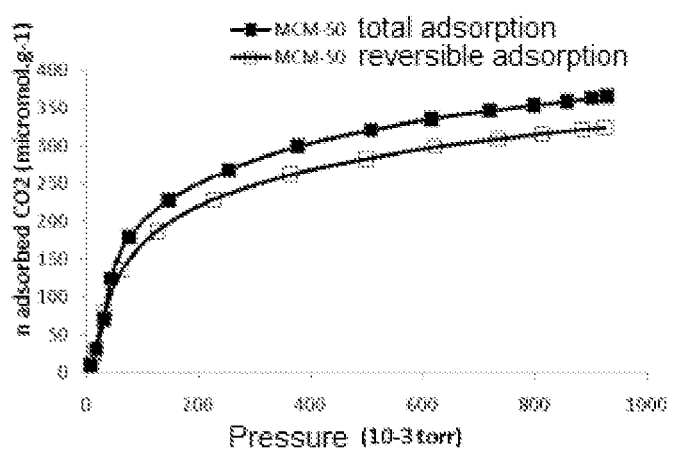
FIG. 7 shows the $CO_2$ adsorption isotherms measured in parallel with the measurement of the $CO_2$ adsorption differential heats with $CO_2$ recovery during the first and second adsorption of $CO_2$ (total and reversible adsorptions respectively).

FIG. 7 shows the $CO_2$ adsorption isotherms measured on [CTA]Si-MCM50 pretreated in vacuo at 30° C. parallel with the measurement of the $CO_2$ adsorption differential heats with $CO_2$ recovery during the first and second adsorption of $CO_2$ (total and reversible adsorptions respectively). While the total adsorption corresponds to an adsorption of 360 micromol·g$^{-1}$ of $CO_2$, the reversible adsorption attains a value very close to 325 micromol·g$^{-1}$ of $CO_2$ i.e. a deviation of less than 10%. This shows that both isotherms may be quasi superposed on [CTA]Si-MCM50 pretreated in vacuo at 30° C.

Since the $CO_2$ adsorption calorimetric curves (both total and reversible) may be superposed and the $CO_2$ adsorption isotherms (both total and reversible) may be superposed on [CTA]Si-MCM50 pretreated in vacuo at 30° C., the conclusion is drawn that adsorption of $CO_2$ on [CTA]Si-MCM50 is reversible.

The invention claimed is:

1. A method for isomerisation of glucose into fructose comprising providing glucose in water in the presence of a solid basic catalyst, wherein the reversibility of the $CO_2$ adsorption isotherms at 30° C. and the differential $CO_2$ adsorption heat, measured at 30° C., comprises between 60 and 110 kJ·mol$^{-1}$, and wherein the catalyst is selected from the group consisting of MgLaO, LaO supported on coal, MgLaO treated with pyridine, MCM48 and MCM50.

2. The method according to claim 1, wherein the catalyst is in an amount of between 0.5 and 100% by weight, based on the weight of glucose.

3. The method according to claim 1, wherein the glucose is in an amount of between 0.5 and 15% by weight, based on the weight of water.

4. The method according to claim 1, wherein the method is applied at a temperature between 75 and 180° C.

5. The method according to claim 1, wherein the method does not comprise thermal pretreatment of the catalyst.

6. The method according to claim 1, wherein the method further comprises a preliminary step for treating the MgLaO catalyst with pyridine.

* * * * *

UNITED STATES PATENT AND TRADEMARK OFFICE
CERTIFICATE OF CORRECTION

PATENT NO. : 9,963,477 B2
APPLICATION NO. : 14/241213
DATED : May 8, 2018
INVENTOR(S) : Essayem et al.

It is certified that error appears in the above-identified patent and that said Letters Patent is hereby corrected as shown below:

On the Title Page

Item (75), Inventors:
Please change:
"Nadine Essayem, Saint Just Chaleyssin (FR); Rodrigo Lopes De Souza, Sen. Camara Rio De Janeiro (BR); Franck Rataboul, Lyons (FR); Cyril Feche, Leyment (FR); Dilson Cardoso, Sao Carlos (BR); Demian Patrick Fabiano, Ouro Branco (BR)"

To:
- Nadine Essayem, Saint Just Chaleyssin (FR); Rodrigo Lopes De Souza, Sen. Camara Rio De Janeiro (BR); Franck Rataboul, Lyons (FR); Cyril Feche, Leyment (FR); Dilson Cardoso, Sao Carlos (BR); Demian Fabiano, Ouro Branco (BR) -

Signed and Sealed this
Seventh Day of May, 2019

Andrei Iancu
*Director of the United States Patent and Trademark Office*